(12) United States Patent
Dietz et al.

(10) Patent No.: US 6,834,149 B1
(45) Date of Patent: Dec. 21, 2004

(54) OPTICALLY CONFINED BIREFRINGENT CHALCOPYRITE HETEROSTRUCTURE DEVICES AND OPERATING METHODS

(75) Inventors: Nikolaus Dietz, Tucker, GA (US); Frank L. Madarasz, Madison, AL (US); David Peter Krivoshik, East Amwell Township, NJ (US)

(73) Assignee: Xoetronics, LLC, Ringoes, NJ (US)

( * ) Notice: Subject to any disclaimer, the term of this patent is extended or adjusted under 35 U.S.C. 154(b) by 201 days.

(21) Appl. No.: 10/228,777

(22) Filed: Aug. 27, 2002

Related U.S. Application Data

(63) Continuation-in-part of application No. 09/501,401, filed on Feb. 9, 2000, now Pat. No. 6,442,319.
(60) Provisional application No. 60/119,295, filed on Feb. 9, 1999, and provisional application No. 60/379,270, filed on Dec. 10, 2001.

(51) Int. Cl.[7] .................................................. G02B 6/00
(52) U.S. Cl. ....................................... 385/122; 385/147
(58) Field of Search ............................... 385/120, 121.1, 385/22, 123, 12–15, 4, 126, 128, 147; 435/6, 91.2; 422/55; 65/409

(56) References Cited

U.S. PATENT DOCUMENTS

| | | | |
|---|---|---|---|
| 4,122,407 A | 10/1978 | Van Vechten | |
| 4,960,319 A | 10/1990 | Dankowych | |
| 5,776,375 A | 7/1998 | Hofstraat et al. | |
| 5,864,641 A | 1/1999 | Murphy et al. | |
| 5,922,537 A | 7/1999 | Ewart et al. | |
| 6,122,305 A | 9/2000 | Putnam et al. | |
| 6,406,845 B1 * | 6/2002 | Walt et al. | 435/6 |
| 6,482,593 B2 * | 11/2002 | Walt et al. | 435/6 |
| 2002/0009719 A1 * | 1/2002 | Walt et al. | 435/6 |

* cited by examiner

*Primary Examiner*—Akm Enayet Ullah
(74) *Attorney, Agent, or Firm*—Mathews, Collins Shepherd & McKay, P.A.

(57) ABSTRACT

An optical quantitative detection device comprising: an optical quantitative detection device comprising: a nonlinear/birefringent waveguide sensor with a top surface for interacting with a target molecule, wherein optical excitation of the sensor enables quantitative, spectral discrimination of the target molecule.

29 Claims, 16 Drawing Sheets

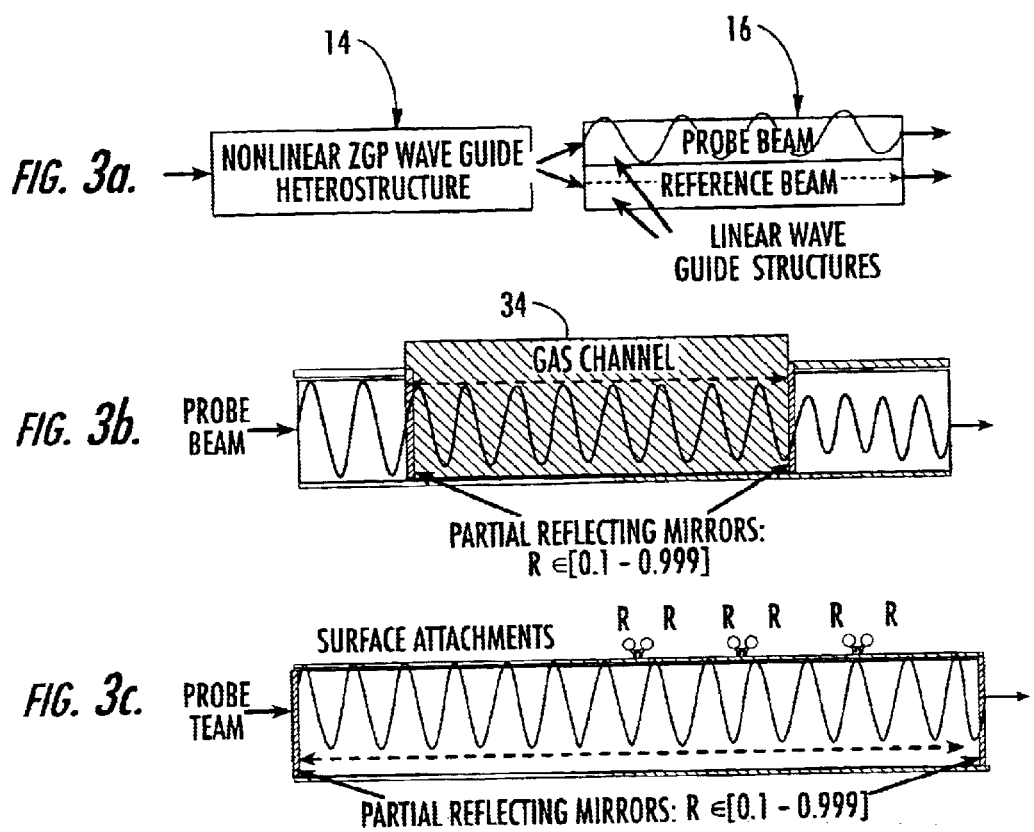

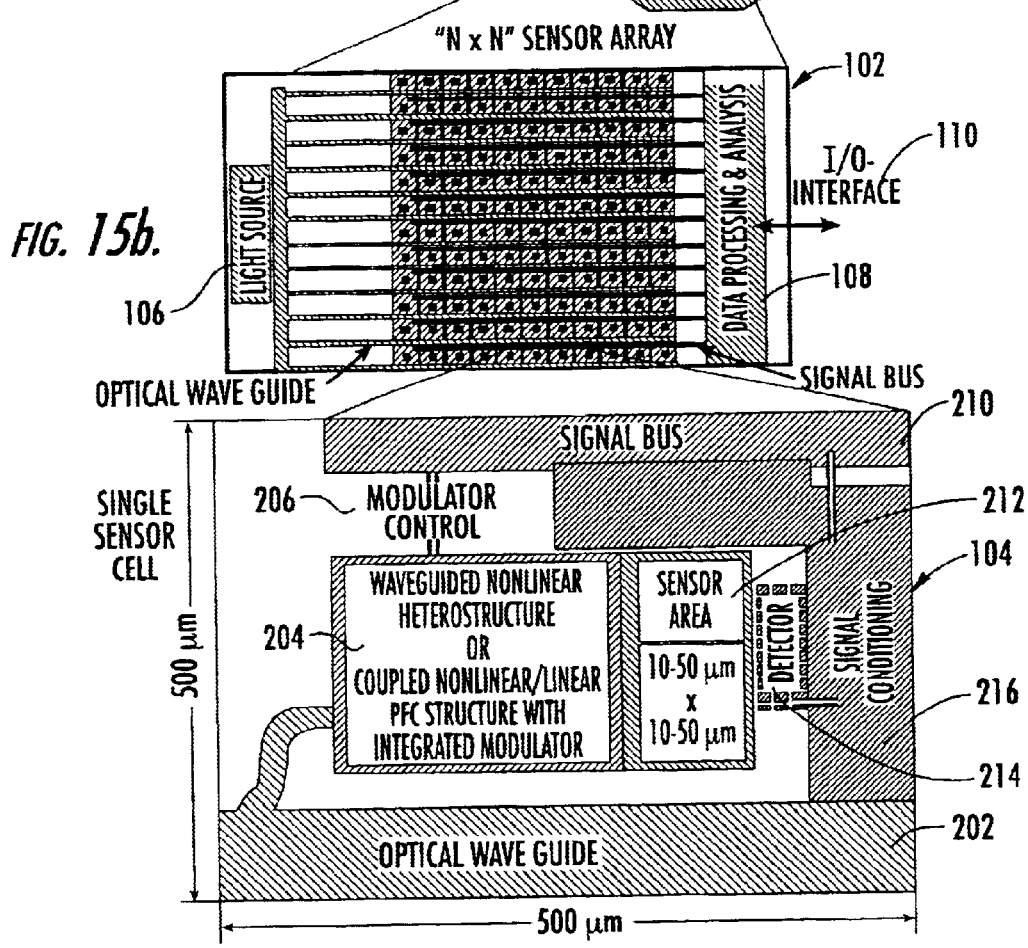

US 6,834,149 B1

OPTICALLY CONFINED BIREFRINGENT CHALCOPYRITE HETEROSTRUCTURE DEVICES AND OPERATING METHODS

CROSS REFERENCES TO RELATED APPLICATIONS

This application is a continuation in part of U.S. patent application Ser. No. 09/501,401 filed on Feb. 9, 2000 now U.S. Pat No. 6,442,319, which claims the benefit of U.S. Provisional Application Ser. No. 60/119,295 filed on Feb. 9, 1999. This application claims the benefit under 35 U.S.C. 119(e) of U.S. Provisional Application Ser. No. 60/339,270, filed on Dec. 10, 2001.

FIELD OF THE INVENTION

This invention relates generally to the optical detection of a target molecule and more particularly to nonlinear waveguides for quantitative determination of the target molecule.

BACKGROUND OF THE INVENTION

Monitoring the levels of various chemical compounds and agents is important for anti-terrorism, environmental monitoring, the diagnosis, treatment and control of diseases as well as in law enforcement. Applications for monitoring include compact self contained sensors, applicable to remote, real-time sensing of trace impurities, such as: greenhouse gases; smog; smoke stack emissions; toxic chemical agents; toxic biological agents; water pollutants; and similar molecules. Additionally there is a significant need in medical applications for the recognition of immobilized biomolecules such as with frequency-agile lasers, and for infrared countermeasures in the defense industry.

SUMMARY OF THE INVENTION

In accordance with the present invention, there is provided an optical quantitative detection device comprising: a nonlinear/birefringent waveguide sensor with a top surface for interacting with a target molecule, wherein optical excitation of the sensor enables quantitative discrimination of the target molecule.

BRIEF DESCRIPTION OF THE DRAWINGS

A more complete understanding of the present invention may be obtained from consideration of the following description in conjunction with the drawings in which:

FIGS. 3a, 3b, and 3c are a detail of the wavelength selection and sensor probe areas;

FIGS. 15a, 15b and 15c show an integrated multi-area sensor module; and,

DETAILED DESCRIPTION OF VARIOUS ILLUSTRATIVE EMBODIMENTS

Figure 1:
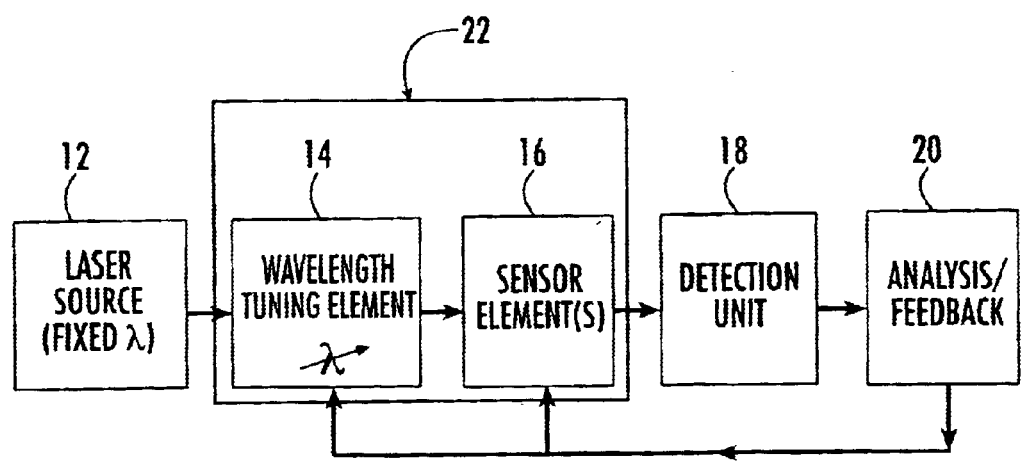
FIG. 1 is a functional block diagram of an integrated sensor arrangement.

Although the present invention nonlinear/birefringent waveguide sensor is particularly well suited for use in chemical/biological (CB) hazard detection including chemical weapon (CW) and biological weapon (BW) detection and shall be so described herein, it is equally well suited for remote, real-time sensing of trace impurities, such as: greenhouse gases; smog; smoke stack emissions; toxic chemical agents; water pollutants; and other environmental components; and it is equally well suited for use in medical applications for the recognition of immobilized biomolecules such as with frequency-agile lasers, and for infrared countermeasures in the defense industry.

The present invention nonlinear/birefringent waveguide sensor is a non-destructive monitoring device, for probing and unambiguously identifying quantitatively a target molecule within a mixed specimen. With operational capabilities incorporating several physically distinct modes of operation the nonlinear/birefringent waveguide sensor has a myriad of monitoring and detection application capabilities.

The development of compact, highly integrated chemical and biological detection systems that will provide accurate, continuous, real-time warnings prior to exposure to a chemical/biological hazard in the environment is of importance not only for chemical weapon or biological weapon detection. In addition, the present invention nonlinear/birefringent waveguide sensor can be used for the monitoring of a variety of potential environmental air/water pollutants, as well as a variety of other chemical/biological monitoring applications. Several optical detection concepts are described utilizing optical fibers and linear waveguided structures. A review of the various techniques is described in *Chemical and Biochemical Sensing with Optical Fibers and Waveguides*, ed. Gilbert Boisdé and Alan Harmer, ISBN 0-89006-737-6; Artech House, Inc, Norwood, Mass. 02062 (1996). However the techniques that are discussed are applicable to a limited particular niche market for a very specific application and lack the potential of further development due to limitations in either integration, handling or discrimination capabilities. Referring to Table 1, there is shown criteria that must be considered for the development of a compact, integrated chemical/biological hazard detection system.

TABLE 1

1) High sensitivity/detection limits;
2) the capability to discriminate/identify known chemical and biological agents;
3) the capability to identify potential harmful (comparison with known structures), but not yet identified chemical and biological agents;
4) self-calibration and adjustable warning- and alarm level functions;
5) robust maintenance and easy exchangeable modules;
6) operational at normal environmental conditions;
7) minimal energy consumption;
8) function reliability and life time, and
9) portability.

There are a variety of applications where large volumes/distances are probed. For the remote sensing of chemical agents, integration is less of importance compared to the efforts on developing high-intense, coherent laser light sources within the atmospheric infrared (IR) transparency window: mid-IR (3–5 microns) and far-IR (8–12 microns). Limitation given through the transparency windows of the atmosphere and the requirement of high-power laser sources generates its own set of diagnostic techniques applied to a small but important group of environmental critical chemical agents. A locally applied chemical/biological hazard sensor has the disadvantage of being able to probe only a limited volume but the advantage, however, of not being restricted to the atmospheric transparence window(s), which leaves the possibility of a wider detection range. In addition, the integration of remote read-out functions in such a locally deployed chemical/biological hazard sensor unit may afford the opportunity to establish a wide-range chemical/biological hazard monitoring network.

The present invention nonlinear/birefringent waveguide sensor is based on birefringent, optically confined nonlinear chalcopyrite (CP) heterostructures that are operated as a tunable (frequency agile) IR laser source as well as an integral part of the chemical/biological hazard detection system. Such a detection system has the advantage to utilize conventional, well-established semiconductor lasers that emit in the visible or near infrared wavelength range with no cooling requirements. The useful transparency region of such a single layered and multiple layered, nonlinear/birefringent, waveguided chalcopyrite heterostructure(s) extends from approximately the near-IR through the far-IR wavelength regime (0.6 $\mu$m through 20 $\mu$m), depending on the chalcopyrite compounds chosen. The wavelength tunability in these chalcopyrite heterostructures allows for the discrimination and identification of almost all molecular structures in a probed medium or attached at a probed interface/surface, using resonant phase sensitive and/or amplitude sensitive detection.

The following illustrates the potential field of applications that can be exploited with optically confined birefringent heterostructures:

OPO applications: 1-dim and 2-dim confined layers for frequency agile laser light generation in the near IR and far IR wavelength range. Vertical and laterial confined device structures for sum—and difference frequency mixing. Use of integrated solid state pump laser with 1–2.7 $\mu$m output or sensitization of probe surface/interface to specific molecules. This provides an integrated solid state molecular sensor (SSMS).

Photonic crystals: 2-dim and 3-dim confined birefringent chalcopyrite layer and nano structures embedded closely lattice matched compound semiconductors or dielectic layers such as $SiO_2/Si_3N_4$, CaF, etc. This provides all Photonic switches; optical communication devices; and, laser light protection devices.

SHG applications (thick layers): use of high power CO2 laser (10.6 $\mu$m), SHG (5.3 $\mu$m), and, FHG (2.7 $\mu$m). This provides chemical gas sensors; air quality monitors; and, counter measures.

Solid-State Molecular Sensor—Nonlinear/birefringent Waveguide Sensor

Referring to FIG. 1 there is shown a schematic representation of a fully integrated nonlinear/birefringent waveguide sensor. The sensor comprises a laser light source 12, nonlinear waveguided heterostructure 14 for wavelength/frequency tuning which can be a single or multiple optical confined chalcopyrite (CP) heterostructure for the generation of coherent IR light (with either a broad IR wavelength output range or an externally controlled tuning range), a sensor element area 16 where selected beam(s) interacts with an interface, a gas volume, or an ambient, a detection unit(s) 18, and an analysis/discrimination unit 20 with integrated feedback logic. The nonlinear waveguided heterostructure 14 and the sensor element area 16 can act collectively as a probe/sensor module 22. All of these components can be either monolithically integrated on one substrate, a hybrid-solution (for example micro-bonded heterostructures), or linked via optical connections (waveguides or optical fibers) to each other in close proximity. The central pieces of the present invention nonlinear/birefringent waveguide sensor are embedded birefringent CP heterostructures, which can be operated either as a tunable IR laser source, or as an integral part of the chemical agent detection system.

The nonlinear waveguided heterostructure 14, the "wavelength tuning element", a key feature of the present invention sensor device, is built up of a birefringent CP layer(s) surrounded by optically confining and guiding cladding layers. A significant difference between the ordinary $n_e$ and extraordinary $n_o$ refraction indices of a birefringent CP layer enables the phase matching in the collinear propagation geometry (the most useful for various applications). For example, if a CP layer is deposited such that the optical axis lies in the plane of the layer, the phase matching is obtained by properly choosing the angle between the optical axis and the propagation direction.

Figure 2A:
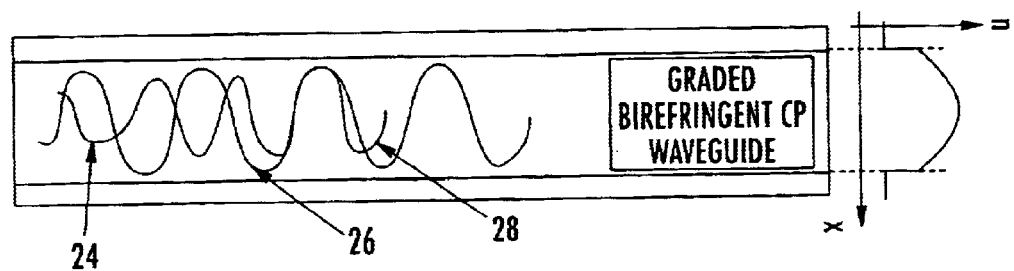
FIGS. 2a and 2b are a schematic illustration of possible multiple layered constructs of an exemplary embodiment of the nonlinear/birefringent waveguide sensor.
Figure 2B:
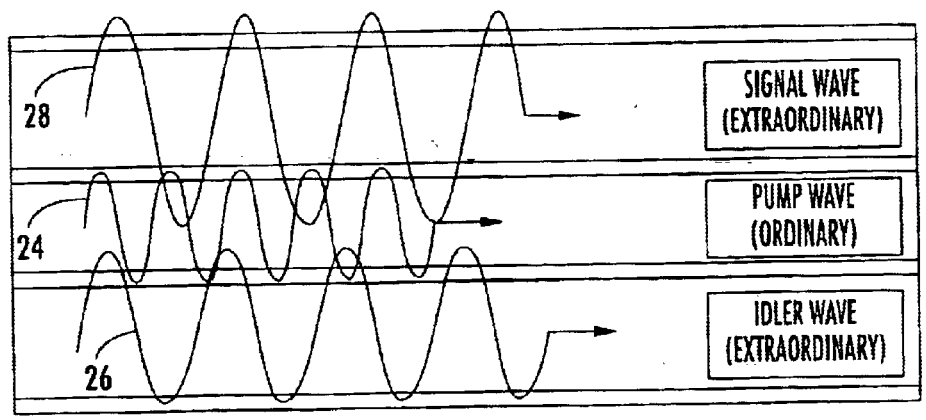

Referring to FIGS. 2a and 2b there is shown a schematic illustration of possible multiple layered constructs of an exemplary embodiment of the nonlinear/birefringent waveguide sensor. The frequency-agile optical parametric generator, based on graded nonlinear waveguide, is illustrated in FIG. 2a. All three participating waves, pump wave (ordinary) 24, idler wave (extraordinary) 26 and signal wave (extraordinary) 28, propagate in spatially overlapping regions of the waveguide, which results in an efficient nonlinear interaction. Their cross extensions (in the growth direction) are schematically indicated as the transversal dimensions of the corresponding waves. Phase matching is achieved by the corresponding choice of the direction of the optical axis of the crystal relative to the propagation direction. A significant advantage is provided by the refractive index graded layers that permit waveguided propagation of the waves of different wavelengths in the same waveguide. As such there is flexibility to either have nonlinear generated waves propagate in the same spatial region as the pump wave or, if desired, to separate them and force them to propagate in different waveguides.

Wave propagation in an exemplary embodiment of the different waveguides is depicted in FIG. 2b. This shows an optical parametric generator based on a triple-waveguide structure with spatial separation of the pump, signal and idler waves. The three waveguides are single-mode, nonlinear, open resonators whose indices and thicknesses are chosen for the corresponding waves, pump wave 24, idler wave 26 and signal wave 28, to propagate as the lowest modes. With the optical axis lying in the plane of the waveguide, phase matching is dependent on the angular orientation between it and the propagation vector of the wave. In addition, it is dependent on the orientation of the polarization of the pump wave 24 with respect to the axis of the guide.

That is, either transverse electric (TE) or transverse magnetic (TM), which governs the effective indices of refraction. FIG. 2b also illustrates the nonlinear interaction of the waves 24, 26 & 28 via the "tunneling" between neighboring waveguides essentially, the overlapping of their evanescent waves. Phase matching and the strength of the interactions depend explicitly on the thickness and geometry of the guide(s). Moreover, this structure has the added flexibility that phase matched coupling can occur between the various modes of the guide, which is absent in bulk materials.

Thus configurations as those shown in FIGS. 2a & 2b add flexibility to the design, manufacturing and operation of the integrated sensors, parametric light sources (fixed-frequency and tunable) and frequency-agile lasers. The control in geometric wave propagation, the planar device design, and the engineering capabilities in the optical confinement of such CP heterostructures provide unique advantages that are absent in the bulk materials. The most evident are mechanical robustness, small size, and weight, which makes the nonlinear/birefringent waveguide sensor useful in airborne and portable devices.

Referring to FIGS. 3a, 3b and 3c there are shown graphic representations of the application of NLO effects in a nonlinear chalcopyrite-based waveguide structure for generating/mixing laser light. Such an application is useful in generating laser light in a wavelength region near a specific resonance frequency of an adsorbed molecule at a surface or a specially prepared interface. With proper waveguide design, this structure will have a precise control of phase matching and frequency interaction and a selection of propagation modes. Here, the sensing element 16 follows sequentially the wavelength tuning element 14 as shown in FIG. 3a, and is constructed as a differential optical sensor. As illustrated in FIGS. 3b and 3c, the upper —probing part—can be exploited for both, the probing of a gas volume, and the probing of attachments to surfaces/interfaces. By using partially reflecting side face, multiple internal reflectance conditions can be used to enhance the overall sensitivity of such a configuration. Such sensitivity enhancement schemes are important, for instance, to identify and analyze complex chemical/biological hazard agents.

Further signal enhancement for specific agents can be included with the nonlinear/birefringent waveguide sensor structure. For example, electric field-modulation of either surface or interface structures are possible to either enhance or suppress the surface reactions of specific agents. Utilizing multiple, coupled waveguided structures will allow phase sensitive wave interference detection that may lead to an all-optical sensor system. Examples of achieving enhanced sensitivity include: electrical or magnetic biasing of active surface/interface for cleaning/reactivating of active surface, ionizing of molecules (enhancing of reactions), and, trapping of molecules; and, electrical field-modulation for either wavelength modulation or for phase sensitive detection.

Fields of applications include: sensors to identify and monitor complex biological structures; medical sensors to identify viruses and diseases; multi-area sensors for medical screening; and, compact multi-area sensors to monitor chemical/biological hazard hazards in the environment.

Figure 5:
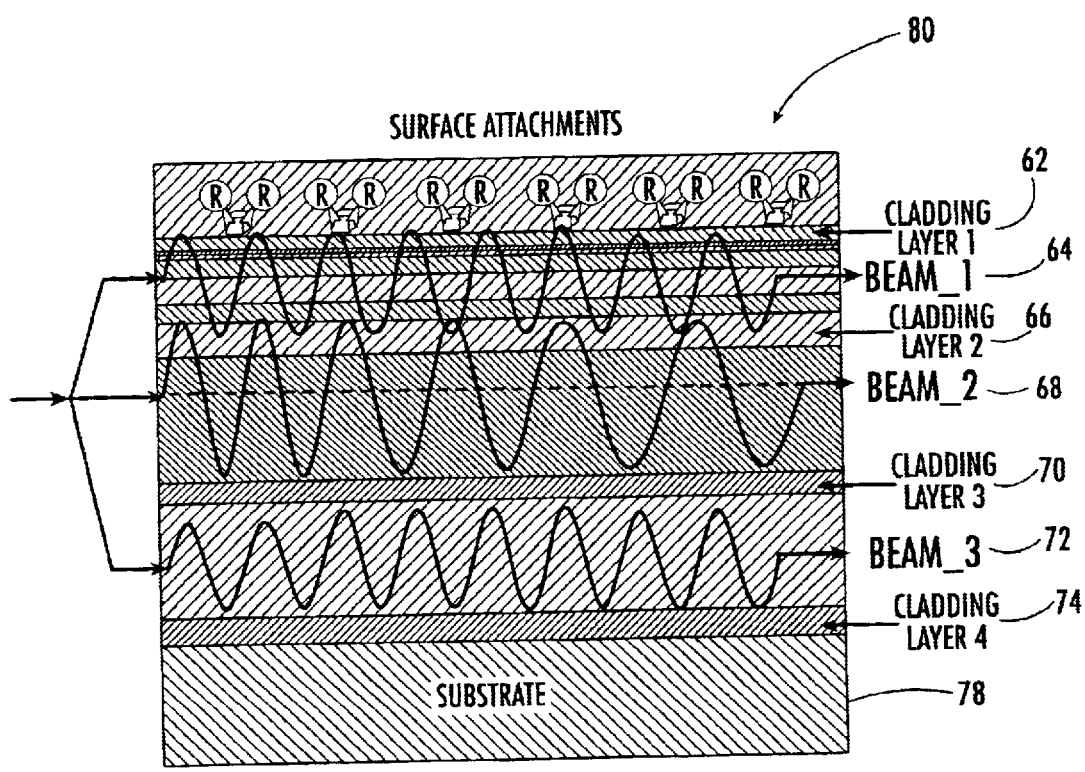
FIG. 5 is a schematic representation of a multiple layered linear/nonlinear waveguided heterostructure.

Of particular interest is an all-optical sensing, discrimination and detection which is outlined in FIG. 5. It is based on the wave separation shown in FIG. 2b. The nonlinear/birefringent waveguide sensor sensing area consist of three interacting waves each predominantly propagating in a separate guide. The spatial overlap of their evanescent waves penetrating into the adjacent guides gives rise to nonlinear interactions. While it is expected that their interactions will be weak, this is compensated for by a high Q factor (low losses) of the waveguides. A principal advantage of this design is that the signal wave is separated from the pump and idler waves, which dramatically decrease background scattering and noise. This feature is especially useful for integrated sensors in the detection and discrimination of specific molecular targets. For such a use, the upper cladding layer 62 in FIG. 5 should be chemically sensitized to allow absorption of specific, targeted molecules. Such a sensitized surface reaction layer will alter its optical dielectric properties upon reaction(s) with a specific molecule, antigen or antibody. The alteration due to the absorbed molecules/structures will perturb the propagation condition of the signal wave and shift the OPO frequency. This frequency shift, though small, can be measured, e.g., by optical beats method that is based on coherency of the signal wave. Accounting for the dielectric properties of the adsorbent molecules will be made by considering them as a composite and using a well-developed method described in M. I. Stockman, K. B. Kurlayev, and T. F. George, "Linear and Nonlinear Optical Susceptibilities of Maxwell Garnett Composites: Dipolar Spectral Theory," Phys. Rev. B 60(24), pp. 17071–17083 (1999). The compact spatial integration capability of such a nonlinear/birefringent waveguide sensor system will foster the development of highly sensitive miniaturized sensor and multi-area sensors that will accelerate the detection of various biochemical and molecular species.

Figure 4:
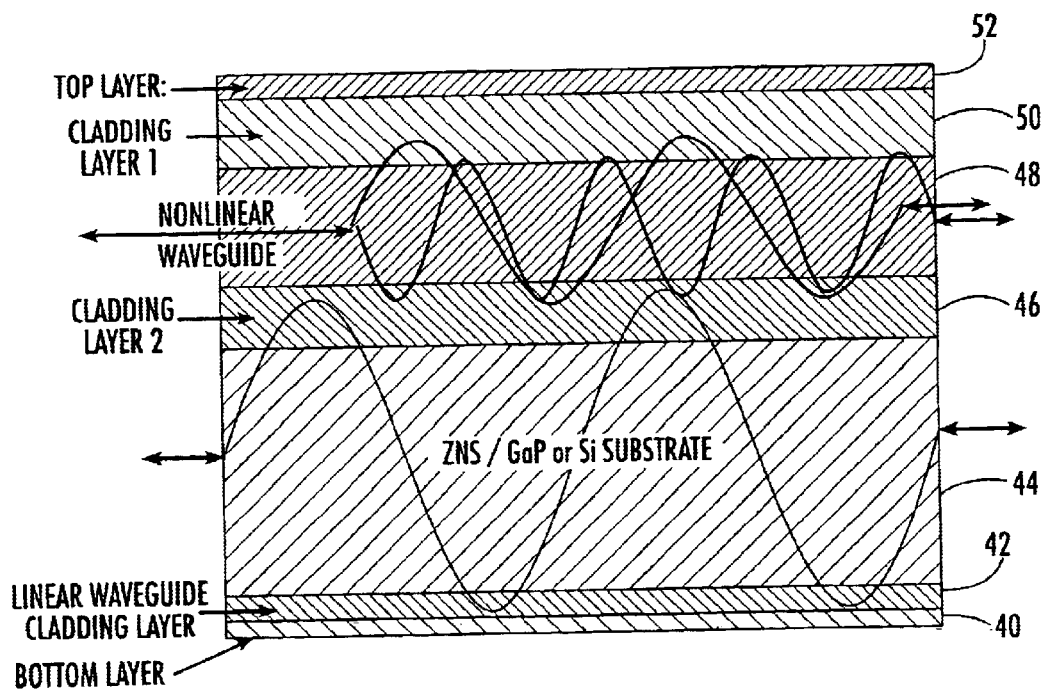
FIG. 4 is a schematic representation of a layered double waveguide heterostructure, where the substrate itself is used as a linear waveguide.

Referring to FIG. 4 there is shown one embodiment of a double waveguided device structure, here a linear— substrate-based waveguide and a nonlinear $ZnGeP_2$ waveguide layer. A bottom layer 40 is covered by a linear waveguide cladding layer 42. A substrate-based waveguide 44 such as ZnS/GaP or Si covers the linear waveguide cladding layer 42 and is covered by a second cladding layer 46. A nonlinear $ZnGeP_2$ waveguide layer 48 is on top of the second cladding layer 46. A first cladding layer 50 is on top of the nonlinear $ZnGeP_2$ waveguide layer 48 and has a top layer 52 on top of it. With proper design of the cladding structure(s) 46 between the two waveguides 44 and 48 (denoted as coupling area), waves propagating in these two waveguides 44 and 48 can interact in the coupling region of the second cladding structure 46. As a result, the NLO frequency generation in the NLO layer can be altered if the wave in the linear layer 44 modulates the optical and electrical properties in the nonlinear waveguided layer 48.

Consider the coupling of two waveguides, for example, the nonlinear/linear waveguide combination (shown in FIG. 4) or a nonlinear/nonlinear waveguide combination. The coupling is analogous to that of two LC circuits or of two coupled pendulums. Consider two waveguides 44 and 48 shown in FIG. 4. When isolated, each waveguide has a separate modal distribution in the xy-plane, which is perpendicular to the waveguiding direction z. Waveguides 44 and 48 support one or more guided modes each. The total electric field solution is a linear superposition of the individual waveguide modes with z-dependent amplitude coefficients as is the total magnetic field solution. These amplitudes satisfy a set of coupled linear differential equations which express the coupling between waveguides 44 and 48, which can be cast in the form of an eigenvalue-eigenfunction problem for the eigenstate solutions of the coupled system of two waveguides. There are two eigenvalue and associated eigenvector solutions for both codirectional and contradirectional couplings. In general, the eigenmode solutions are either in-phase or out of phase. The power transfer from one waveguide to another can be either synchronous or asynchronous depending on whether waveguides 44 and 48 are similar or not.

Coupled mode theory for anisotropic waveguides is known to those skilled in the art. Further information can be found in the following publications, which are incorporated herein by reference: D. Marcuse, Bell Syst. Tech. J. 54, 985–995 (1975); A. Hardy, W. Streiffer, and M. Osinski, Opt. Lett. 11, 742 (1986); and L. Tsand and Sl. Chuang, J. Lightwave Technol. and IEEE J. Quantum Electron. 6, 832 (1988).

Because waveguide directional couplers can perform power division, modulation, switching, frequency selection, and polarization selection, a number of unique devices can be constructed with a double waveguide structure. For example, a modification/altering at the $ZnS_{1-x}Se_x/SiO_2/Si_3N_4$ interface surface (see for instance first cladding layer 62 shown in FIG. 5) will change not only the phase condition and amplitude of Beam 1, but will also change the wave interaction/propagation (Beam 2) in the nonlinear waveguide layer 68. Setting the proper phase matching conditions, the phase shift and amplitude changes of Beam 1 can be translated into a frequency shift of the light generated in the nonlinear waveguide(s) 68. This enables the building of highly phase-sensitive surface detectors, where surface induced phase changes are analyzed by a frequency shift in Beam 2. Referring to FIG. 5 there is shown an illustration of a sensor device structure 80 built up from multiple waveguide structures. Beam 1 is the probe beam, which interacts with the surface/interface to sense surface attachments/modifications. Beam 3 is a reference beam embedded in the cladding layers 3 and 4, with a defined phase and amplitude correlation to Beam 1. Beam 1 and Beam 2 are coupled via the second cladding layer 66, which allows interactions between both beams 1 and 2 as well as a modification of the properties in the third cladding layer 70 and the underlying nonlinear waveguide layer by Beam 1. Phase and/or amplitude changes in Beam 1 upon surface attachments/modifications 60 can be analyzed by Beam 2 and by comparing Beam 1 with Beam 3. The detection process can involve an interference process of the beams with each other.

The development and optimization of optically confined birefringent CP heterostructures as well as the physical understanding of optical interactions in confined birefringent heterostructures and optically coupled multiple heterostructures, is importance for the nonlinear/birefringent waveguide sensor. The next step requires the establishment of optical data bases containing spectral dependent absorption energies of chemical/biological hazard agents (optical fingerprints), their optical absorption strengths and attachment probabilities on selected surfaces, and the design for optimum bonding and specificity of surfaces with regard to specific agents. These efforts are crucial to obtain: the optical cross-sections and attachment factors; the input parameters for the design and optimization of surface attachment layers; an assessment of achievable and required device sensitivities; and, the required input parameters for device design criteria.

Bulk and Structural Properties of III-IV-$V_2$ Chalcopyrites

The potential of ternary III-IV-$V_2$ bulk chalcopyrite compound semiconductor materials for nonlinear optical applications have been studies intensively during the last decades. Although the CP semiconductors have electrical and optical properties comparable or superior to their group IV, III-V or II-VI counterparts, for many applications they have advantages due to their lower crystal symmetry. Being optically birefringent and pleochroic their optical and electro-optical properties are highly orientation dependent, thereby making them more sensitive to their environment. In principle, it enables new capabilities, especially in thin-film coupled-waveguide devices, where the possibility of controlling layer compositions, thicknesses, and spacings is expected to lead to new levels of performance in linear and nonlinear devices.

Figure 6:
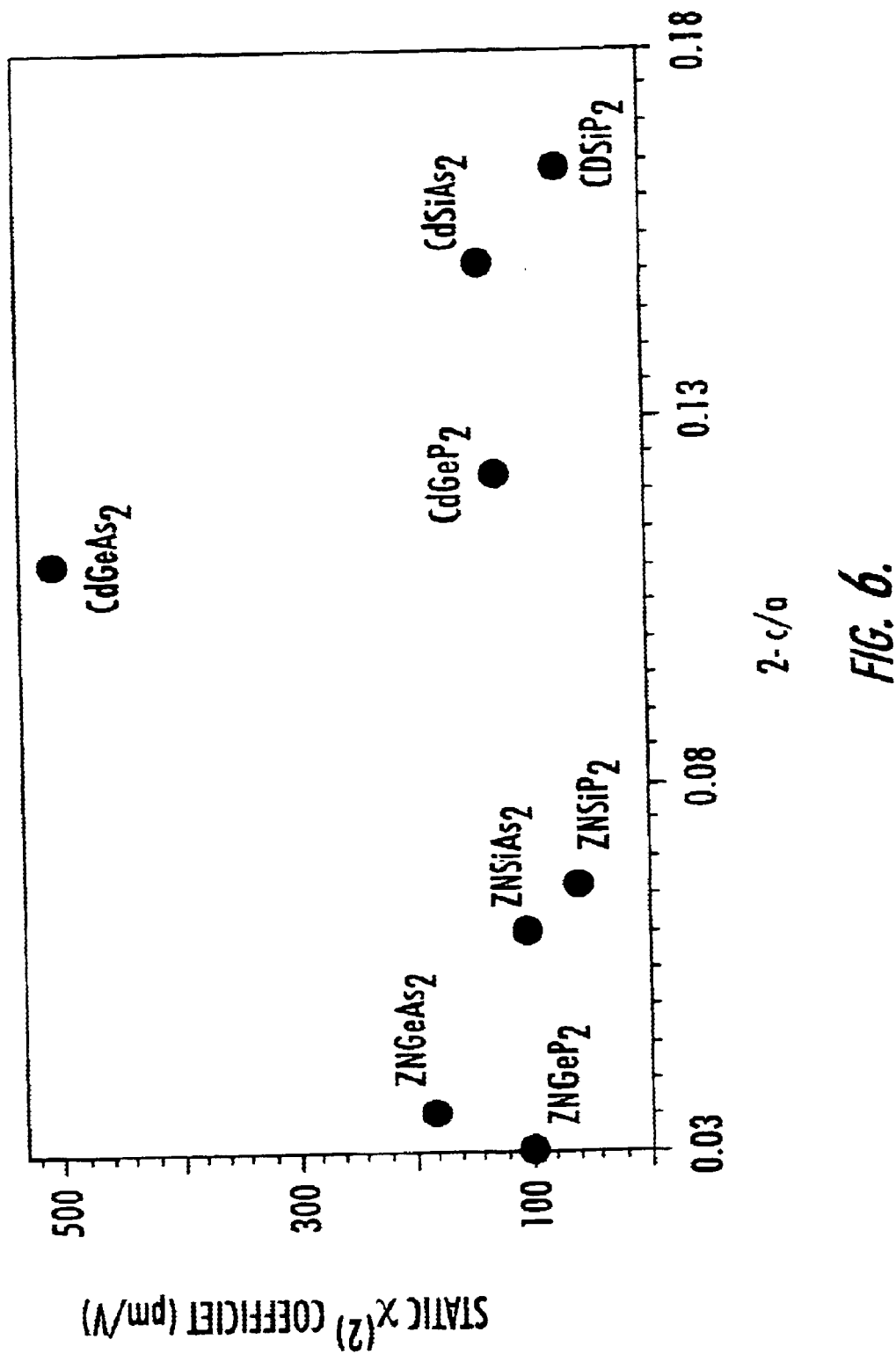
FIG. 6 is a graph of nonlinear optical coefficients $\mu^{(2)}$ for the chalcopyrite compounds $Cd(Ge_{1-x}Si_x)(As_{2-y}P_y)$ and $Zn(Ge_{1-x}Si_x)(As_{2-y}P_y)$.

The highest nonlinear coefficients in the class of III-IV-$V_2$ semiconductors are reported for the compound systems $(Zn_{1-x}Cd_x)GeAs_2$, $Zn(Ge_{1-x}Si_x)As_2$ and $Zn(Ge_{1-x}Si_x)P_2$. As depicted in FIG. 6, all these systems have a positive birefringence. The associated second-order nonlinear susceptibility, $\mu^{(2)}$, increases correspondingly with the substitution of As for P, Ge for Si and Cd for Zn. $CdGeAs_2$ is reported to have the highest nonlinear optical coefficient in the class of of phase-matchable compounds. Note that even the low lying compound $ZnGeP_2$ has a nonlinear optical coefficient approximately 160 times greater than KDP, making it one of the most efficient nonlinear crystal for use in the wavelength range 0.7–12 $\mu$m.

Figure 7:
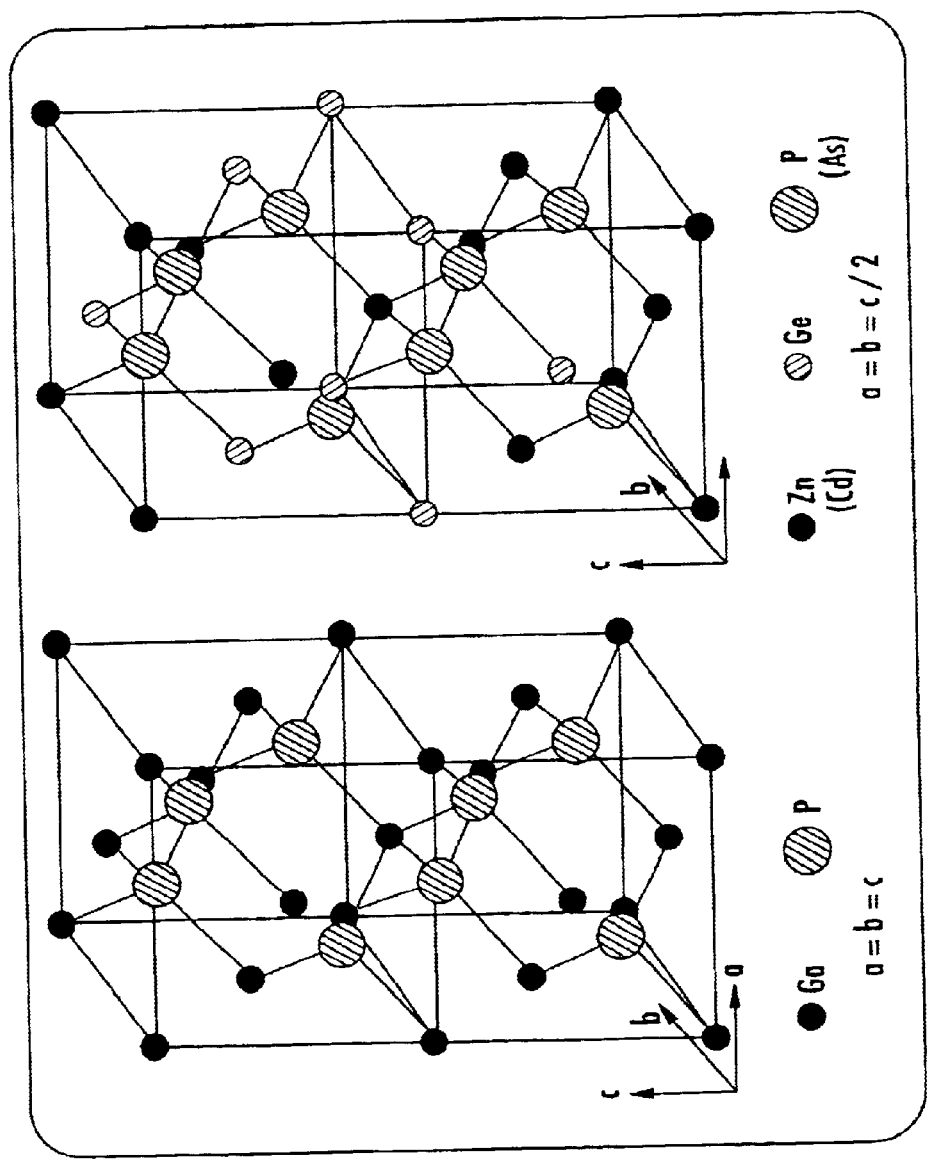
FIG. 7 is a schematic model of crystal structures for GaP (zincblende) and for $ZnGeP_2/CdGeAs_2$ (chalcopyrite structure)

The III-IV-$V_2$ class of compound semiconductors, space group $\overline{I42}d$, are the isoelectric analogues of the zincblende gallium phosphide (GaP), space group $\overline{F43}m$, whereby, the average number of bonding electrons per atom remains unchanged. For this reason they are known as pseudo III-V compounds. The unit cells of the CP compounds $ZnGeP_2$ and $CdGeAs_2$, shown in FIG. 7, have a total of 16 atoms: four zinc (cadmium), four germanium and eight phosphorus (arsenide) atoms. The analogous zincblende structure of GaP is of a similar construction, but its unit cell has a total of eight atoms (four cations and four anions) with equal a, b, c lattice parameters.

The ordered arrangement of the two cation species, tetrahedrally coordinated to the anion atoms, in chalcopyrite unit cell leads to twice the c-axis height of the analogous zincblende cell. However, the differences in the two cationic species surrounding the anion and the manner of ordered substitution accounts for a peculiar distortion in the c-axis. $ZnGeP_2$ and $CdGeAs_2$, in which a=b>c/2, have slight compressions along the c-axis a=5.463 Å, c/a=1.966[14] and a=5.943 Å, c/a=1.888[14], respectively. These compressions have a pronounce effect on their observed nonlinear electrical and optical properties.

Materials selection considerations for optical confined III-IV-V$_2$ CP heterostructures The development of thin-film growth techniques for the CP materials is of critical importance not only to extend the unique nonlinear properties of bulk CP materials to a wider range of applications, but also improve the nonlinear optical properties of bulk materials and device structures. Next to the availability of high-quality, lattice-matched substrates, the following selection criteria must be examined carefully: nonlinear figure of merit; a large, transparent wavelength range (0.6 $\mu$m≦λ≦20 $\mu$m) for nonlinear optical interactions; the availability of lattice-matched cladding layer to optically confine the CP heterostructures; tuning of refractive indices in graded index CP heterostructures, cladding layers, and coupled, multiple heterostructures; and, stringent control of composition, stoichiometry, point defect chemistry as well as extended defect formation and propagation are required for the fabrication of heterostructures with sufficiently good optical quality.

Figure 8:
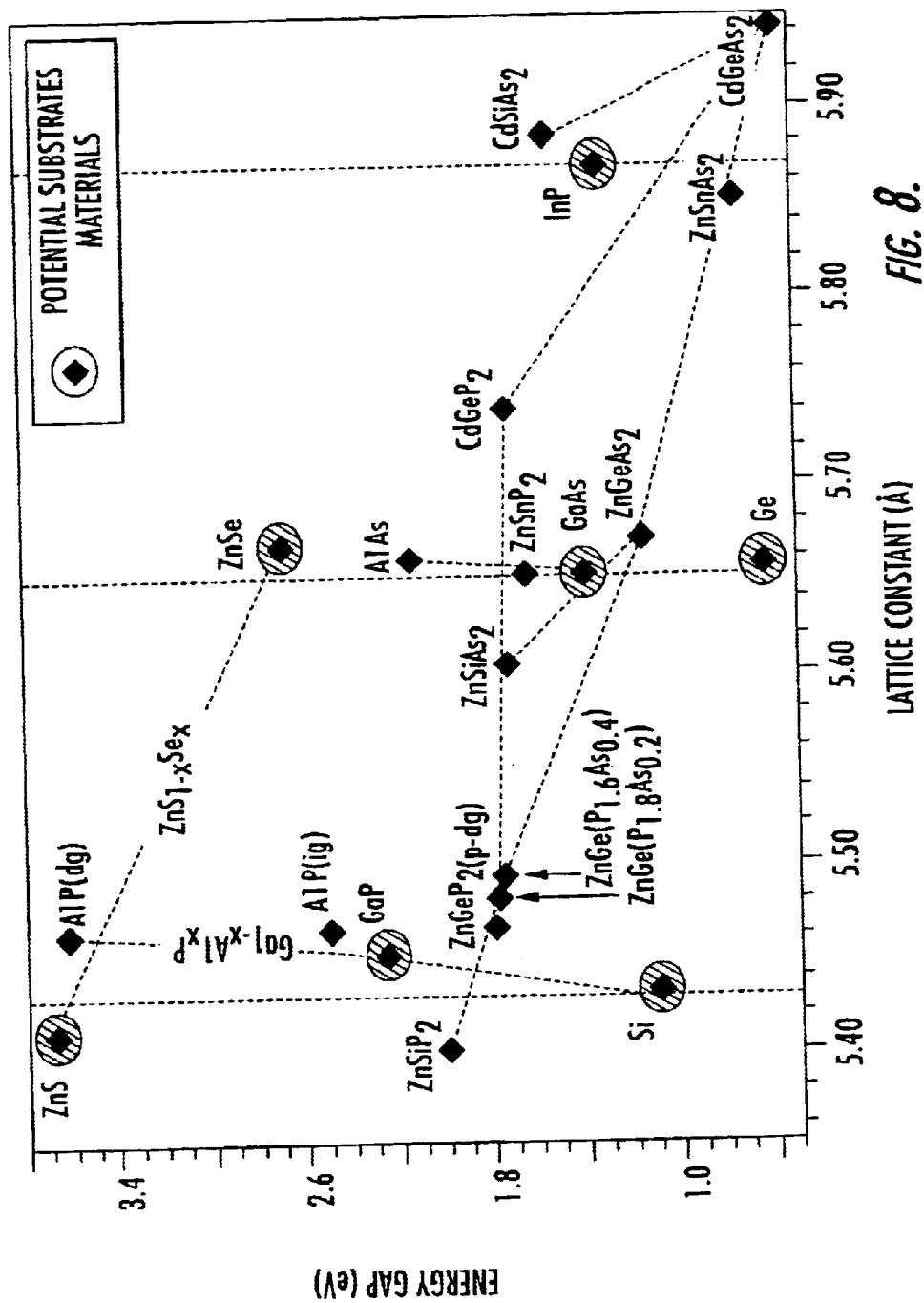
FIG. 8 is a graph of energy gaps and lattice constants for the selected III-IV-$V_2$ CP compounds in relation to group IV, III-V and II-VI semiconductors (dg: direct gap, ig: indirect gap, p-dg: pseudo-direct gap)

FIG. 8 summarizes the lattice constants and band gap energies of several CP materials, together with the lattice constants and band gap energies of potential group IV-, III-V-, and II-VI substrates. From this, it appears that lattice-matched growth conditions for stoichiometry controlled quaternary CP materials systems may be possible for three materials systems: $(Cd_{1-x}Zn_x)GeAs_2$ or $CdGe(As_{2-x}P_x)$ on InP substrates; $Zn(Ge_{1-x}Si_x)As_2$ or $ZnGe(As_{2-x}P_x)$ on GaAs substrates, with lattice-matching cladding layers formed by compositionally controlled $GaAs_{1-x}Al_x$ layers; and, $Zn(Ge_{1-x}Si_x)P_2$ on GaP, or Si substrates, with lattice-matching cladding layers made from compositionally controlled $GaP_{1-x}Al_x$ or $ZnS_{1-x}Se_x$ layers.

The lack of any lattice-matching and optically confining cladding materials for $(Cd_{1-x}Zn_x)GeAs_2$ or $CdGe(As_{2-x}P_x)$ compounds on InP will make these systems extremely difficulty to work with and to manufacture high quality multiple heterostrucutres. However, because of their high optical nonlinearities, these compounds may have potential applications in quantum confined nonlinear optical nano-structures and in strained layered heterojunction optical devices.

The nearly lattice-matched growth of $ZnGeAs_2$ on GaAs substrate by organometallic chemical vapor deposition (OMCVD) has been investigated. Studies show that high-quality p-type $ZnGeAs_2$ layers can be grown on (100) GaAs. Compared to the bulk crystal, a larger c/a ratio was observed, which may result in a reduction of the birefringence in these layers. Unfortunately, no detailed information concerning the birefringent properties was given. And most recently, theoretical studies on the structural and electronic properties of $ZnGeAs_2$ and $ZnGeAs_2/GaAs$ superlattices have been done.

Figure 9:
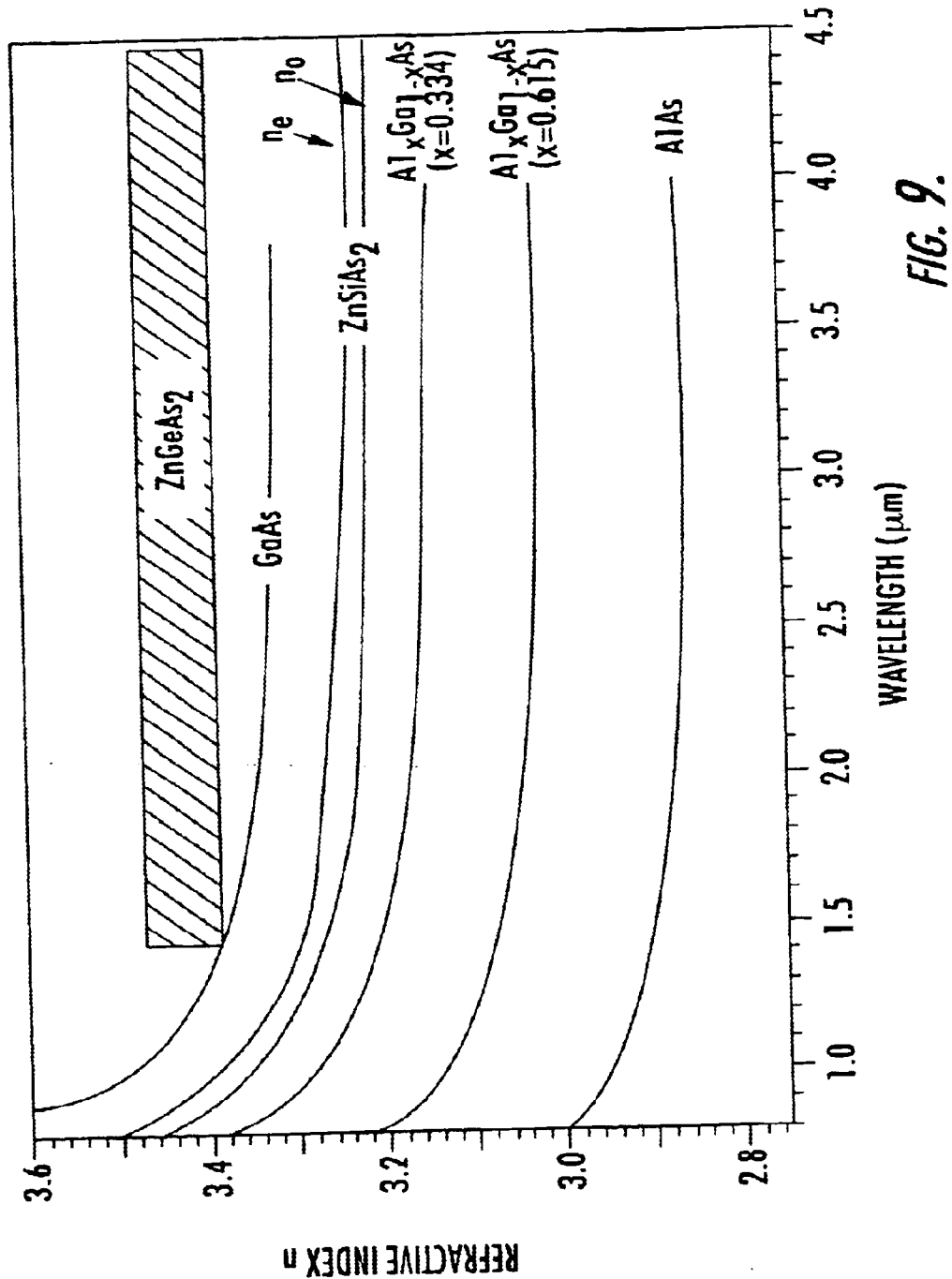
FIG. 9 is a graph of refractive index of $Al_xGa_{1-x}As$ below the band gap as a function of composition x[19], together with refractive index data for $Zn(Ge_{1-x}Si_x)As_2$.

The formation of operational nonlinear optical waveguided $ZnGeAs_2$ heterostructures clearly depends on knowledge of the below bandgap indices of refraction. However, precise values are presently undetermined. FIG. 9 shows the refractive index of $Al_xGa_{1-x}As$ as a function of below band gap excitations for various compositions, x, of Al. Superimposed on this plot are the ordinary, $n_o$, and extraordinary, $n_e$, indices of refraction of $ZnSiAs_2$, which is birefringent. Also shown is the region of refractive indices for $ZnGaAs_2$. A value of 12.3 for the high frequency dielectric constant, $\epsilon_\infty$, which corresponds to a refractive index of $n_\infty=3.507$ has been reported. If this value is considered together with the dependence of the refractive index on lattice-matched $Al_xGa_{1-x}As$ layers depicted in FIG. 9, it suggests optical confined $Al_xGa_{1-x}As/ZnGeAs_2/$ . . . multiple heterostructures, with $ZnGeAs_2$ as an embedded, active birefringent layer.

The third system, $ZnGeP_2$—$ZnSiP_2$ on GaP, or Si substrates is of special interest. It combines a high nonlinear optical figure of merit with the availability of a lattice-matched optical confinement layers and the potential of integrated optoelectronic structures on Si substrates. The total variation of the a-axis lattice parameter at room temperature in the $ZnGeP_2$—$ZnSiP_2$ system ranges from 5.399 Å–5.465 Å, and thus straddles the lattice constants of both GaP (5.4512 Å) and silicon (5.431 Å).

Figure 10:
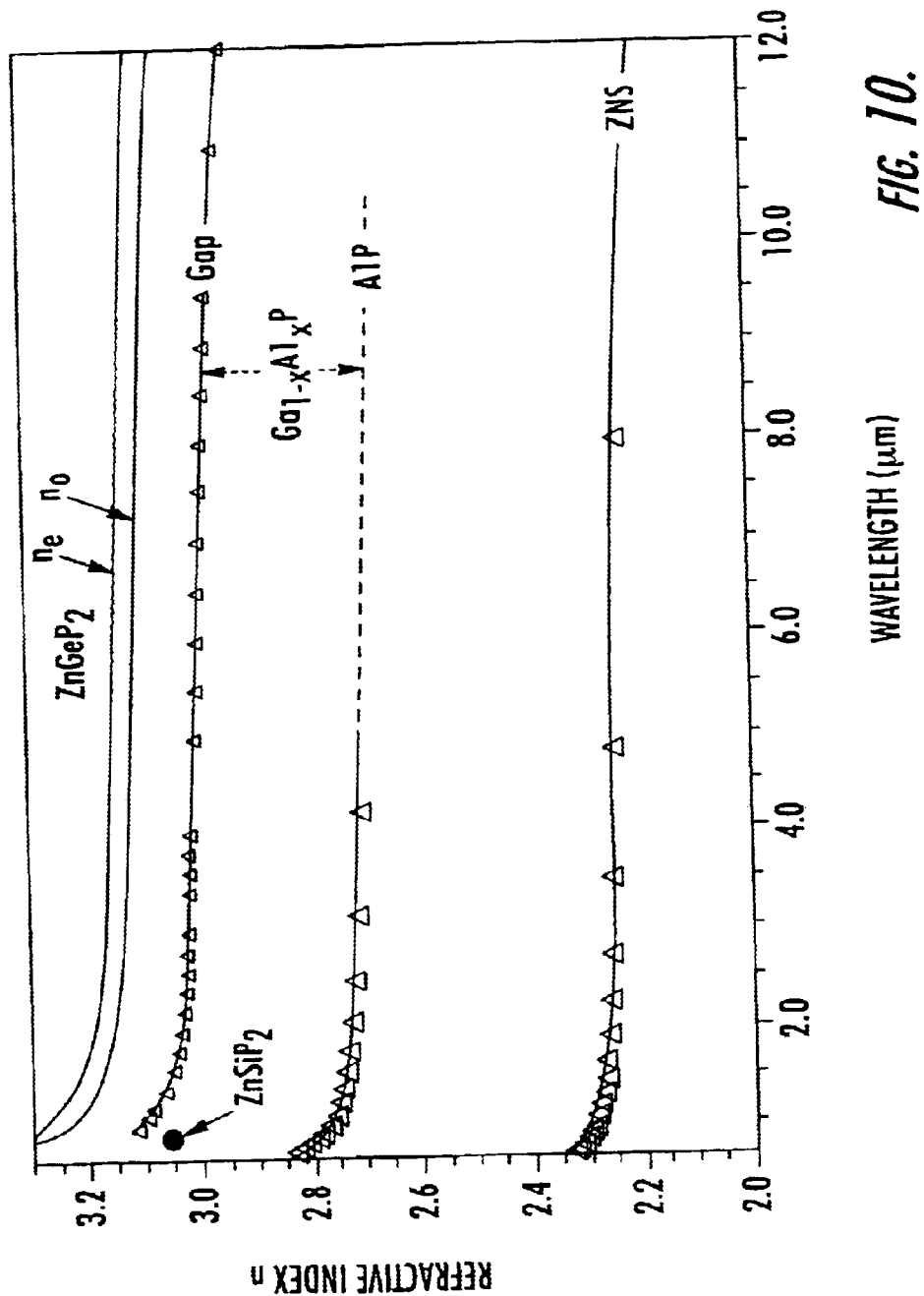
FIG. 10 is a graph of refractive index values for the birefringent CP material system $Zn(Ge_{1-x}Si_x)P_2$ and potential optical cladding materials.

Refractive index values for the birefringent CP material system $Zn(Ge_{1-x}Si_x)P_2$ and potential optical cladding materials GaP, AlAs, $Ga_{1-x}Al_xP$ or ZnS grown lattice-matched on GaP and/or Silicon substrates are show in FIG. 10. The lattice constant of $Ga_{1-x}Al_xP$ as a function of Al composition, x, varies from a=5.45120 Å at x=0 (GaP) to a=5.46350 Å at x=1 (AlP). Note that this is a lattice mismatch of only 0.2% over the entire composition range. The change in composition allows for the tuning of the refractive index to up to 8%. With this, $Ga_{1-x}Al_xP$ is an ideal optical confinement layer for the higher indexed birefringent $ZnGeP_2$ or $Zn(Ge_{1-x}Si_x)P_2$ layer.

Only two values of refractive indices have been reported for $ZnSiP_2$: n=3.31 at 600 nm and n=3.06 at 900 nm. The direct energy gap in this compound was calculated at 2.98 eV, and modulated reflectance spectra on $ZnSiP_2$ show the first direct transition occurs at 2.97 eV followed by another strong transition at 3.06 eV. These values correspond to ($\Gamma_4$, $\Gamma_5$)–>$\Gamma_1$, respectively.

Another cladding materials system is $CaF_2$. This system is also closely lattice-matched to Si at temperature (a=5.46306 Å). $CaF_2$ provides for an even larger difference in refractive index, n=1.4288 to n=1.3989 over the range of 1 $\mu$m to 5 $\mu$m, respectively, and has transparency region from 0.1 $\mu$m to 10 $\mu$m. In addition, it can serve as a better diffusion barrier than GaP and $ZnSi_xGe_{1-x}P$. However, because of the large electronegativity of fluorine, significant differences are expected in the initial stages of the epitaxial growth when $ZnGeP_2$ is grown on $CaF_2$ coated with Si as opposed to when it is grown directly on $CaF_2$. The expected differences must be carefully studied experimentally.

Figure 11:
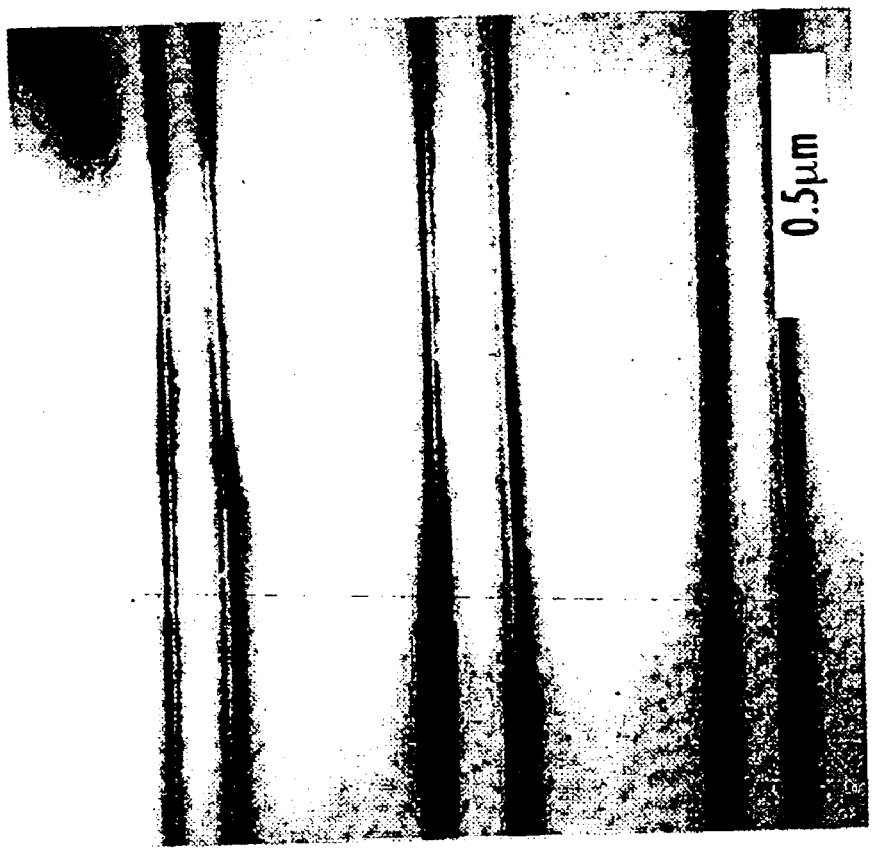
FIG. 11 is a cross-sectional TEM bright field image of a multiple $GaP/ZnGeP_2$ heterostructure grown on a (001) GaP substrate photograph.

FIG. 11 shows a cross-section of the transmission electron microscopy (TEM) bright field image of a multiple GaP/$ZnGeP_2$ heterostructure grown on a (001) GaP substrate. It is illustrative of the junction quality that may be achieved in growth. It also demonstrates the feasibility of manufacturing high-grade GaP—$Zn(Si_xGe_{1-x})P_2$, Si—$Zn(Si_xGe_{1-x})P_2$ single hetero-structures and $Ga_{1-x}Al_xP$—$Zn(Si_xGe_{1-x})P_2$ multiple heterostructures which, in fact, were grown several years ago[31–37]. The growth of these heterostructures on (001) and (111) GaP and Si substrates was accomplished by organometallic chemical vapor deposition (OMCVD), utilizing dimethylzinc (DMZ), diluted germane(0.33%), phosphine(10%) and disilane(0.2%) in $H_2$ as source materials. At growth temperatures around 580° C., high-quality epitaxial layers with mirror smooth surfaces were produced. TEM and secondary ion mass spectrometry (SIMS) of the GaP—$ZnGeP_2$—GaP multi-heterostructures showed sharp interfaces between the layers and high purity of the epilayers as compared to bulk $ZnGeP_2$ single crystals grown by directional solidification. The TEM and SIMS analysis also revealed the formation of extended defects, while electrical measurements revealed intrinsic point defects dominated the p-type conductivity. Experience tells us that both can be minimized through a careful and refined materials development effort. These challenges become even more crucial in the quaternary $Zn(Si_xGe_{1-x})P_2$ system, which allows the growth of exact lattice matched heterostructures on silicon.

Figure 12:
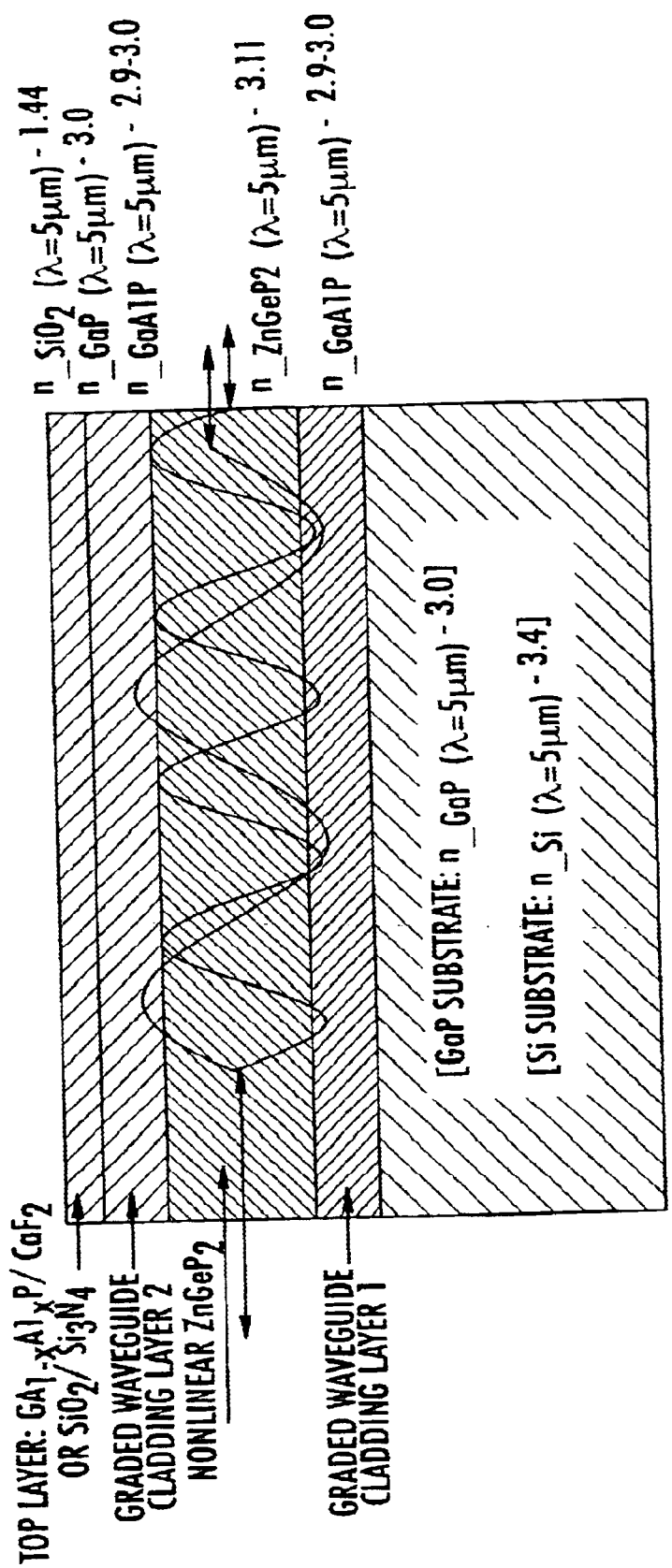
FIG. 12 is a vertical schematic of layered multiple heterostructures, containing a birefringent waveguided layer embedded between two lower indexed cladding layers.

Recent advances in real-time monitoring and control of OMCVD processes make it possible to control defect formations, their interactions and propagation during the later stages of heteroepitaxy growth. Defect formations are strongly coupled to the kinetics of heteroepitaxial growth. By virtue of this fact, they are closely related to surface structure that depends on both reconstruction and the nature and distribution of defects in the epitaxial film. So far, the progress in understanding and controlling thin film growth has been very slow, since little is known about chemical reaction pathways and reaction kinetics parameters during the decomposition process of the organometallic precursors FIG. 12 depicts schematically a planar nonlinear waveguided $Zn(Si_xGe_{1-x})P_2$ heterostructure, embedded in optically confining cladding layer, grown either on Si, GaP, and/or ZnS substrates. The choice of substrate and the subsequent deposited layers have to be closely lattice matched and, at the same time, provide the proper refractive index to guide the waves in the above $Zn(Si_xGe_{1-x})P_2$ layer(s). Such optically confined birefringent layers offer advantages in tuning capability and phase matching, which can greatly enhance the operational characteristics of frequency-agile IR laser light generation. Potential combinations of closely lattice-matched heterostructures, capable to optically confine a birefringent $ZnGeP_2$ or $Zn(Si_xGe_{1-x})P_2$ active layer, are summarized in Table 2.

parametric oscillation (OPO) and second harmonic generation (SHG), are limited by the phase-matching requirements of the bulk material. For example, $ZnGeP_2$ would make an excellent frequency doubler of 10.6 μm radiation (yielding 5.3 μm radiation) but the phase matching conditions are difficult to achieve, which in turn places severe limitations on its conversion efficiency. The extraordinary wave index of refraction of $ZnGeP_2$ at 10.6 μm is almost exactly equal to the ordinary wave index of refraction at 5.3 μm making phase matching in bulk material marginal at best. This limitation, and corresponding limitations for other nonlinear processes, can be avoided by incorporating the $ZnGeP_2$, or other appropriate CP materials, in a waveguide structure. For example, the phase matching region for SHG can be considerably extended by coupling the pump into the guide in the fundamental, m=0, mode and phase matching to the m=2 mode of the second harmonic.

In order to achieve phase-matched conditions they considered that the optical axis of the $ZnGeP_2$ lies in the plane of the guide. In that case the angle between the direction of propagation of the wave in the guide and the optical axis of the guide material can be adjusted to achieve the phase matching condition. As shown below, they found that this can be accomplished for both SHG and OPO in $ZnGeP_2$ guides on GaP. Moreover, the waveguide geometry affords an additional opportunity for phase matching not available in bulk material. It is possible to couple radiation between different modes of the guide. They found that this can greatly extend the wavelength region over which phase-matched SHG can be achieved in a planar waveguide of $ZnGeP_2$.

If the optical axis of the, uniaxial, nonlinear guide material lies in the plane of the guide, optical propagation in the

TABLE 2

Materials Selection for optically confined $Zn(Ge_{1-x}Si_x)P_2$ layers.

| No. | Substrate | 1 Cladding layer: Substrate <-> waveguide | Active birefringent layer | 2 Cladding layer: waveguide <-> top |
|---|---|---|---|---|
| 1 | GaP | $Ga_{1-x}Al_xP$ (x = 0–0.5) | $ZnGeP_2$ | $Ga_{1-x}Al_xP$ (x = 0–0.5) & thick GaP top layer |
| 2 | GaP | $Zn(Ge_{1-x}Si_x)P_2$ (x = 0–0.5) | $ZnGeP_2$ | $Zn(Ge_{1-x}Si_x)P_2$ & thick GaP top layer |
| 3 | Silicon | $Zn(Ge_{1-x}Si_x)P_2$ (x = decreasing) | $ZnGeP_2$ | $Zn(Ge_{1-x}Si_x)P_2$ & thick GaP top layer |
| 4 | Silicon | GaP followed by $Zn(Ge_{1-x}Si_x)P_2$ (x = decreasing) | $ZnGeP_2$ | Graded $Zn(Ge_{1-x}Si_x)P_2$ layer with increasing x |
| 5 | Silicon | GaP followed by $Zn(Ge_{1-x}Si_x)P_2$ (x = 0–0.5) | $Zn(Ge_{1-x}Si_x)P_2$ fixed or graded composition | $Ga_{1-x}Al_xP$ (x = 0–0.2) & thick GaP top layer |

The availability of large high quality substrates along with lattice-matching considerations favors the use of Si-substrates. However, the growth on a GaP substrate has the advantage that its lower refractive index, compared to $ZnGeP_2$, acts at the same time as a cladding layer for the waveguide heterostructure. The engineering of optically abrupt or graded confinement structures can be achieved in compositional graded $Ga_{1-x}Al_xP$ layers with negligible lattice-mismatch within the heterostructures. To achieve optical confined heterostructures with larger differences in the refractive indices, the lattice-matched growth on a ZnS substrate is possible with $ZnS_{1-x}Se_x$ confining cladding layers. The feasibility of such heterostructures has to be explored experimentally.

Theoretical Background

Chalcopyrite compound semiconductors are being used to achieve wavelength agility through much of the infrared spectrum. However, many applications, such as optical guide will be governed by two indices of refraction, one of which is dependent on the direction of propagation. If the wave is polarized perpendicular to the guide, transverse magnetic (TM) mode, the index of the guide will be related to the ordinary index of the guide material. This index is independent of the direction of propagation and is referred to as $n_{TM}$. If the wave is polarized in the plane of the guide, transverse electric (TE) mode, the index will depend on the direction of propagation with respect to the optical axis of the guide material. This index is referred to as $n_{TE}$.

Using the standard equations for step index waveguides, $n_{TM}$, and $n_{TE}$ are given by, $$kt(n_O^2 - n_{TM}^2)^{1/2} = \qquad (1)$$
$$(m+1)\pi - \tan^{-1}\left(\frac{n_S^2(n_O^2 - n_{TM}^2)^{1/2}}{n_O^2(n_{TM}^2 - n_S^2)^{1/2}}\right) - \tan^{-1}\left(\frac{n_C^2(n_O^2 - n_{TM}^2)^{1/2}}{n_O^2(n_{TM}^2 - n_C^2)^{1/2}}\right),$$

$$kt(n^2 - n_{TE}^2)^{1/2} = \qquad (2)$$
$$(m+1)\pi - \tan^{-1}\left(\frac{(n^2 - n_{TE}^2)^{1/2}}{(n_{TE}^2 - n_S^2)^{1/2}}\right) - \tan^{-1}\left(\frac{(n^2 - n_{TE}^2)^{1/2}}{(n_{TE}^2 - n_C^2)^{1/2}}\right),$$

$$\left(\frac{1}{n}\right)^2 = \left(\frac{\cos\theta}{n_O}\right)^2 + \left(\frac{\sin\theta}{n_E}\right)^2, \qquad (3)$$

$n_O$ and $n_E$ are the ordinary and extraordinary wave indices of the bulk guide material, $n_S$ is the index of the substrate material, $n_C$ is the index of the cladding, t is the guide thickness, $k=2\pi/\lambda$ is the free space wave vector of the radiation, and m is the mode number for the wave in the guide. In addition, $\theta$ is the angle between the propagation direction and the optical axis of the guide material.

Using equations 1–3 and a knowledge of $n_O$, and $n_E$, for the guide material, $n_S$ for the substrate, $n_C$ for the cladding as a function of wavelength, and choosing a value of guide thickness and propagation direction one can calculate the values of $n_{TM}$, and $n_{TE}$ for the guide. These can then be used to obtain the phase matching conditions for the different nonlinear processes.

They chose to examine the specific examples of OPO and SHG Type I phase matching in a ZnGeP$_2$ planar waveguide on a GaP substrate and with GaP cladding. The optical, or z-axis, of the ZnGeP$_2$ lies in the plane of the guide as does the x-axis or y-axis for the optimum Type 1 non-linear coupling. For SHG Type I phase matching they considered that the guide is pumped in the TE mode with propagation at an angle $\Theta$ with respect to the optical axis of the ZnGeP$_2$. Phase matching occurs for the angle $\Theta$ when $$n_{TE}(2\lambda) = n_{TM}(\lambda) \text{ Type } I, SHG. \qquad (4)$$

For OPO Type I phase matching they considered that the guide is pumped in the TM mode with propagation at a angle $\Theta$ with respect to the optical axis of the ZnGeP$_2$. Phase matching occurs for the angle $\Theta$ when $$\frac{1}{\lambda_P} = \frac{1}{\lambda_S} + \frac{1}{\lambda_I} \quad \text{Type I, OPO} \qquad (5)$$

where $\lambda_P$ is the wavelength of the pump, $\lambda_S$ is the wavelength of the output signal, and $\lambda_I$ is the wavelength of the idler wave, and $$\frac{n_{TM}(\lambda_P)}{\lambda_P} = \frac{n_{TE}(\lambda_S)}{\lambda_S} + \frac{n_{TE}(\lambda_I)}{\lambda_I} \quad \text{Type I, OPO.} \qquad (6)$$

Figure 13:
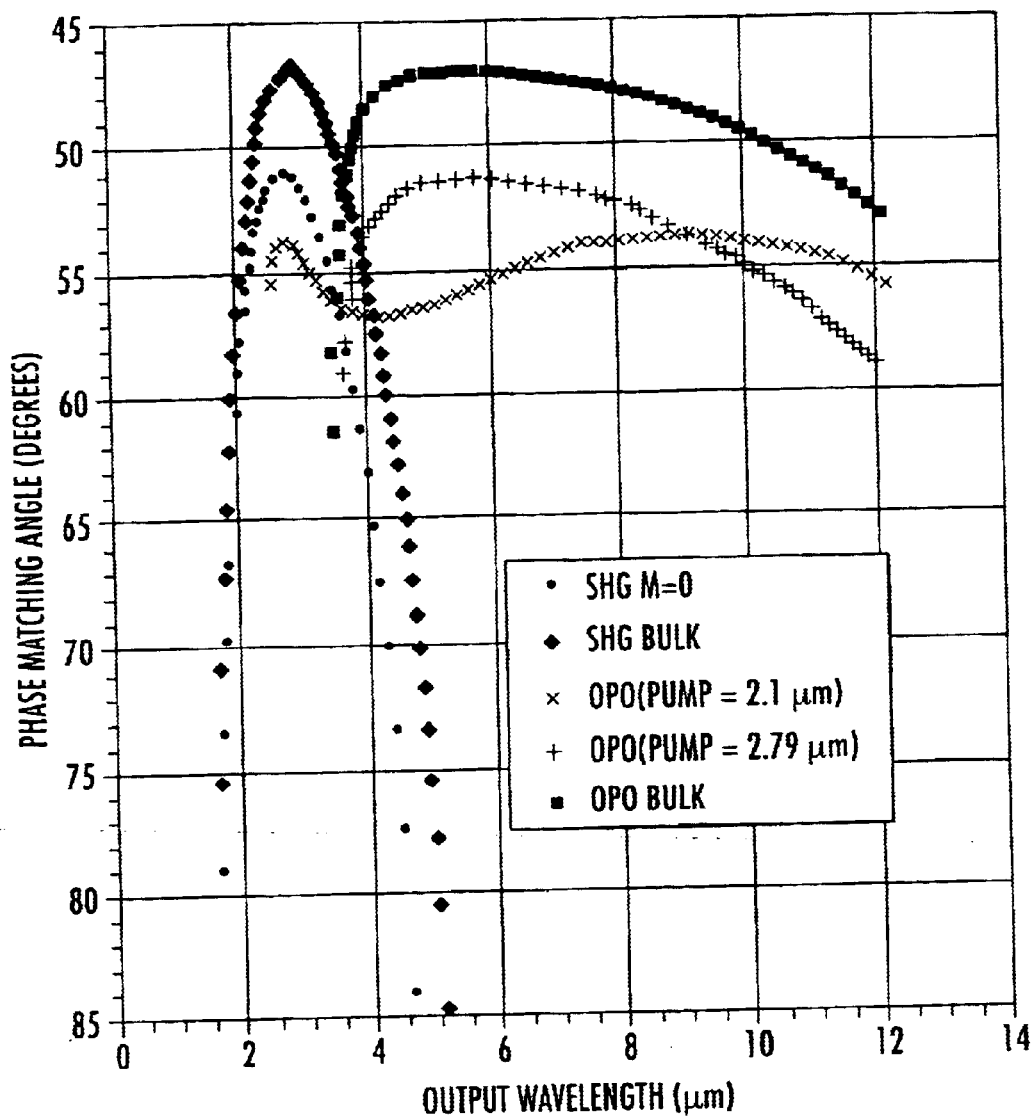
FIG. 13 is a graph of calculated phase matching angles for SHG and OPO in a 16 $\mu$m $ZnGeP_2$ waveguide with a GaP substrate and cladding layer compared with similar curves for bulk material.

Using fits to the literature values for the ordinary and extraordinary indices of bulk ZnGeP$_2$[20] and GaP and equations 1–6 they calculated the phase matching angles shown in FIG. 13 for SHG and OPO for a 16 $\mu$m planar ZnGeP$_2$ guide on GaP operation in the m=0 mode.

The corresponding phase matching angles for bulk ZnGeP$_2$ are shown for comparison. These results show phase matching angles quite similar to those of bulk ZnGeP$_2$ as would be expected for a guide this thick. This simply shows that phased matched SHG and OPO should be readily obtainable in waveguides of ZnGeP$_2$ operating in the m=0 mode. The applicability of the bulk indices for the waveguide will depend on the guide thickness, method of growth, degree of doping, lattice mismatch and internal strain. Bulk indices should be a good approximation for a well constructed 16 $\mu$m thick guide with reasonable lattice match as could be obtained with ZnGeP$_2$ on GaP.

Figure 14:
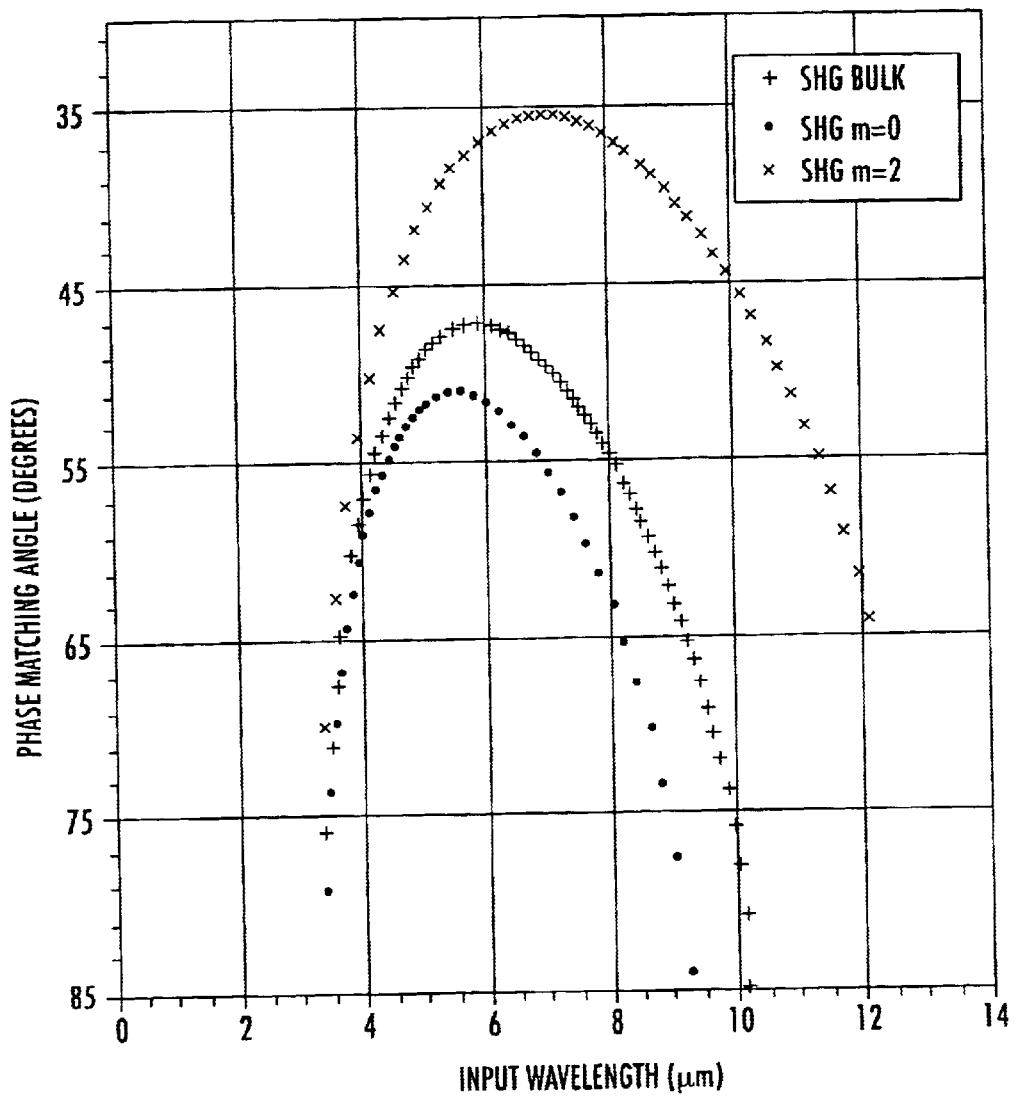
FIG. 14 is a graph of calculated phase matching angles for SHG in the 16 $\mu$m $ZnGeP_2$ waveguide of FIG. 13 pumped in the m=0 mode with output in the m=2 mode compared to the m=0 to m=0 coupling of FIG. 13 and that of the bulk material.

They also examined the case where coupling into the guide occurs in one mode of the guide, the nonlinear process within the guide couples energy to another mode and coupling out of the guide occurs from the second mode. Even though they did not do a detailed calculation of the strength of coupling, they estimated that nonlinear coupling from the m=0 to the m=2 mode, could be as large as 20% of the coupling to the m=0 mode of the guide for similar phase matching conditions. For the purpose of illustration, they considered the case of SHG where the input wave is in the m=0 mode with the second harmonic output considered in the m=2 mode. In this case, they used the value of $n_{TM}(\lambda)$ for the m=2 mode but $n_{TE}(2\lambda)$ for the m=0 mode. Their resulting phase matching angle is plotted in FIG. 14 along with the SHG curve from FIG. 13 and for the bulk material for comparison. Note that in this case phase matching for SHG can be obtained over wider wavelength region than for m=0 to m=0, or for bulk ZnGeP$_2$.

Multi-area Sensor

Figure 16A:
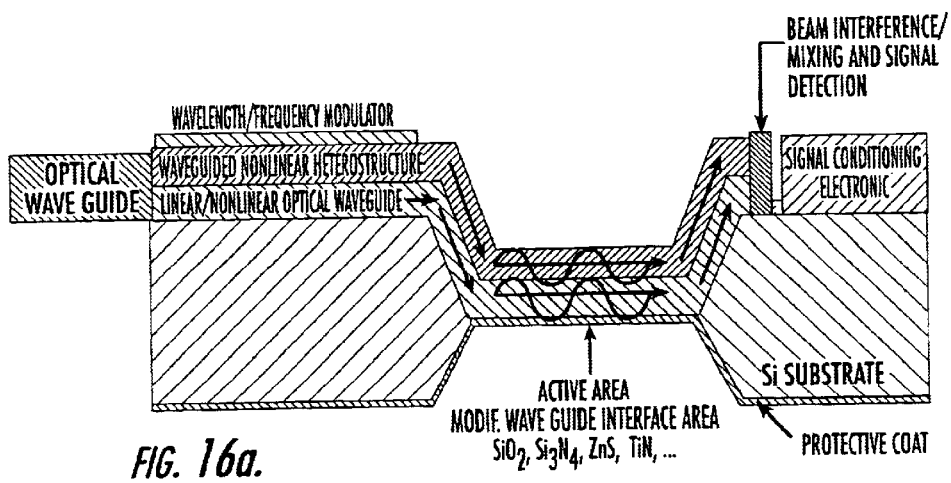
FIGS. 16a and 16b are a cross-sectional view of the integrated multi-area sensor cell.
Figure 16B:
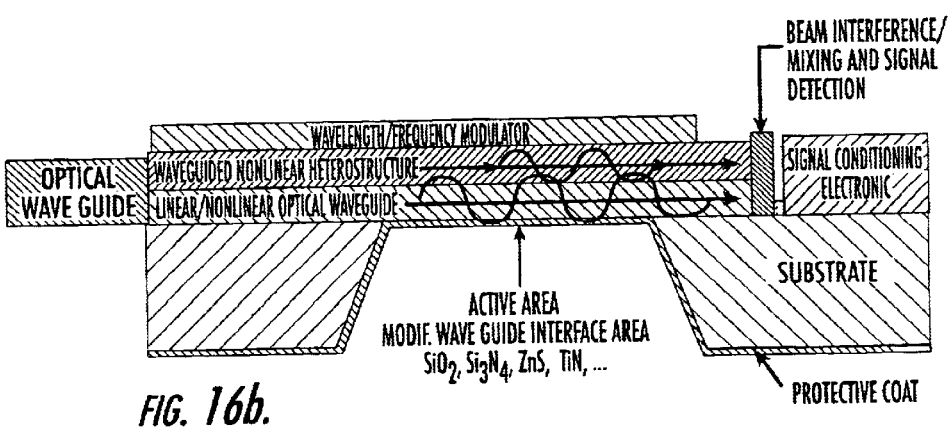

Referring to FIGS. 15a, 15b, 15c, 16a and 16b there is shown schematically an integrated multi-area sensor module, wherein each sensor-cell can be prepared/sensitized for one specific molecular structure, allowing the screening of a sample in investigation to a series possible reactions. FIGS. 16a and 16b show a cross-sectional view of the integrated multi-area sensor cell. FIG. 15a is a schematic representation of a silicon wafer 100 containing a plurality of sensor modules 102. FIG. 15b is a detailed schematic view of the sensor module 102 containing an "N×N" array of sensors 104, light source 106, data processing and analysis module 108 and I/O interface 110. FIG. 15c is a detailed schematic view of a single sensor cell 104 approximately 500 $\mu$m square containing an optical wave guide 202, waveguided nonlinear heterostructure or coupled nonlinear/linear PFC structure with integrated modulator 204, modulator control 206, signal bus 210, sensor area 212, detector 214 and signal conditioning 216.

The integrated multi-area sensor module can be adapted to detect an air borne indication of the target molecule, a chemical agent, a biological agent, a pesticide, and a variety of other target molecules. Additionally, the sensor can be a part of a process control system where the detection of the target molecule is used to provide feedback to the process control.

Summary

The Solid-State Molecular Sensor (present invention nonlinear/birefringent waveguide sensor) system is based on optically confined, birefringent II-IV-V$_2$ compound semi-conductor technology. Its application targets the recognition of chemicals and biological molecules in an ambient environment. Sensing and discrimination of chemical agents is achieved by monitoring and analyzing the nonlinear optical interactions in optically confined II-IV-V$_2$ heterostructures and the probing of linear/nonlinear optical evanesce wave coupling of interface with attached agents. At least two II-IV-V$_2$ CP materials systems, Zn(Ge$_{1-x}$Si$_x$)As$_2$ and Zn(Ge$_{1-x}$Si$_x$)P$_2$, that are suitable for such a nonlinear/birefringent waveguide sensor system. Both systems will allow for the construction of optically confined birefringent heterostructures, closely lattice-matched onto readily available group IV, III-V or II-VI substrates. Waveguided birefringent heterostructures based on the Zn(Ge$_{1-x}$Si$_x$)As$_2$ system will have the potential advantage of a monolithic integrated all optical sensor. At present, however, little is know about the linear and nonlinear optical properties of this material system. This aspect, together with optoelectronic integration aspects favors at present the development of optically confined birefringent $Zn(Ge_{1-x}Si_x)P_2$ layers on GaP and silicon substrates. This material system is also favored because of its larger optical transparency window.

The growth of such structures can be accomplished by OMCVD, which is particularly suited for II-IV-$V_2$ epitaxy, because of access to well developed source vapor compounds for this class of materials, and for nearly lattice matched III-V compounds, serving as substrates and confinement layers in multiple heterostructures. A combination of OMCVD and liquid phase epitaxy (LPE) might be suitable for thicker optical confined birefringent layers.

The theoretical analysis of phase matching in these nonlinear, birefringent heterostructures when applied to the specific guide material $ZnGeP_2$ on a GaP substrate showed that this structure has the added flexibility that phase matched coupling can occur between the various modes of the guide. Moreover, the coupling is a function of the guide thickness. These added degrees of freedom will allow for high gain under conditions where it is difficult or impossible to achieve in bulk material. The results also indicate, among other things, that $ZnGeP_2$ waveguides with harmonic output in the m=2 mode can be used for efficient SHG from input radiation around 10.6 $\mu$m where bulk efficiencies in this wavelength range are too small to be useful.

In view of the foregoing description, numerous modifications and alternative embodiments of the invention will be apparent to those skilled in the art. Accordingly, this description is to be construed as illustrative only and is for the purpose of teaching those skilled in the art the best mode of carrying out the invention. Details of the structure may be varied substantially without departing from the spirit of the invention, and the exclusive use of all modifications, which come within the scope of the appended claim, is reserved.

What is claimed is:

1. An optical quantitative detection device comprising:
a nonlinear waveguide sensor having a top cladding layer with a top surface for interacting with a target molecule;
a second waveguide;
a second cladding layer optically coupling the nonlinear waveguide sensor to the second waveguide, wherein optical excitation of the sensor and optical excitation of the second waveguide enables quantitative spectral discrimination of a target molecule.

2. The optical quantitative detection device as recited in claim 1 further comprising a molecule specific sensitized surface layer on top of the cladding layer whereby a molecule specific binding of a target molecule is provided.

3. The optical quantitative detection device as recited in claim 1 wherein a nonlinear/birefringent waveguided heterostructure is used for frequency agile infrared wavelength generation.

4. The optical quantitative detection device as recited in claim 1 wherein interface induced phase and amplitude changes are coupled back in the underlying nonlinear waveguide for analysis.

5. The optical quantitative detection device as recited in claim 1 wherein interface/surface induces amplitude and phase shifts of an evanescence wave is coupled nonlinearly to another wave(s) propagating in an adjacent, birefringent waveguide(s).

6. The optical quantitative detection device as recited in claim 1 wherein an evanescence wave is coupled nonlinearly to another wave propagating in an adjacent birefringent waveguide.

7. The optical quantitative detection device as recited in claim 1 wherein adjacent waveguides are coupled nonlinearly between mixed modes between waveguides.

8. The optical quantitative detection device as recited in claim 1 wherein induced spectral amplitude and phase shifts couple nonlinear with adjacent waveguided, birefringent layer(s) and modifies phase matching conditions for frequencies generated in an optical parameter oscillator (OPO) process.

9. The optical quantitative detection device as recited in claim 1 wherein the nonlinear waveguide sensor further comprises a nonlinear waveguided layer composed of a multiple-quantum well (QW) structures containing at least one chalcopyrite compound.

10. The optical quantitative detection device as recited in claim 1 wherein the nonlinear waveguide sensor further comprises a nonlinear waveguided layer composed of ordered and/or disordered nano-composites that result in a nonlinear, birefringent layer, even though the compounds for themselves have linear optical properties.

11. The optical quantitative detection device as recited in claim 1 wherein the nonlinear waveguide sensor further comprises a nonlinear waveguided layer composed of ordered and/or disordered nano-composites containing at least one chalcopyrite compound.

12. The optical quantitative detection device as recited in claim 1 wherein the nonlinear waveguided heterostructures are intentionally doped (nonlinear active medium as well as surrounding cladding layers) to form electrical junctions, which are able to control the NLE and NLO properties of the device structure.

13. The optical quantitative detection device as recited in claim 1 wherein the nonlinear waveguided layers comprise chalcopyrite alloys $Zn(Ge_{1-x}Si_x)P_2$ on GaP, or Si, with lattice-matching cladding layers made from compositionally controlled $GaP_{1-x}Al_x$ or $ZnS_{1-x}Se_x$ or CdF layers.

14. The optical quantitative detection device as recited in claim 1 wherein the nonlinear waveguided layers comprise chalcopyrite alloys $Zn(Ge_{1-x}Si_x)As_2$ or $ZnGe(As_{2-y}P_y)$ on GaAs, with lattice-matching cladding layers formed by compositionally controlled $GaAs_{1-x}Al_x$ layers.

15. The optical quantitative detection device as recited in claim 1 wherein the nonlinear waveguided layers comprise birefringent chalcopyrite alloys with cladding layers formed by compositionally controlled dielectric and/or organic layers providing optical guidance.

16. The optical quantitative detection device as recited in claim 1 wherein the nonlinear waveguided layers comprise self-assembled and/or nano-scale engineered chalcopyrite nano-composites containing II-IV-$V_2$ chalcopyrite compounds such as $Zn(Ge_{1-x}Si_x)P_2$, $Zn(Ge_{1-x}Si_x)As_2$, $ZnGe(As_{2-y}P_y)$, or $CdGe(As_{2-y}P_y)$ on embedded in closely lattice-matching III-V, II-VI or I-VII compounds and covered by optically guiding cladding layer(s).

17. The optical quantitative detection device as recited in claim 1 wherein the nonlinear waveguided layers comprise self-assembled and/or nano-scale engineered chalcopyrite nano-composites containing II-IV-$V_2$ chalcopyrite compounds embedded in strained multilayers made from III-V, II-VI or I-VII compound semiconductors.

18. The optical quantitative detection device as recited in claim 1 wherein the nonlinear waveguided layers comprise doping/alloying of the nonlinear active medium made up of II-iV-V2 chalcopyrite compounds to engineer the nonlinear electrical (NLE) and nonlinear optical (NLO) properties of the active medium, the doping/alloying being internal by engineered native defect chemistry, external by adding nonactive elements, or both internal and external whereby the nonlinear electrical (NLE) and nonlinear optical (NLO) properties can be manipulated.

19. The optical quantitative detection device as recited in claim 1 wherein the nonlinear waveguided layers comprise self-assembled and/or nano-scale engineered III-V and II-VI nano-composites embedded in closely lattice-matching III-V, II-VI or I-VII compounds forming a nonlinear, birefringent layer.

20. The optical quantitative detection device as recited in claim 1 wherein the nonlinear waveguided layers comprise growth of the described waveguided heterostructures (a) through (g) by organometallic chemical vapor deposition (OMCVD or MOCVD), by liquid phase epitaxy (LPE), by chemical beam epitaxy (CBE), and/or by gas source molecular beam epitaxy (MBE).

21. The optical quantitative detection device as recited in claim 2 wherein the molecule specific sensitized surface layer comprises ultra-thin metal layers (4–50 Å) such as Au, Ag, Pt.

22. The optical quantitative detection device as recited in claim 2 wherein the molecule specific sensitized surface layer comprises Ultra-thin dielectric layers (5–100 Å) such as $Si_3N_4$—$SiO_2$ $Si_xO_{2-x}$.

23. The optical quantitative detection device as recited in claim 2 wherein the molecule specific sensitized surface layer comprises an organic coating deposited on top of the cladding layer and/or the nonlinear layer.

24. The optical quantitative detection device as recited in claim 1 wherein photonic band-gap crystal arrangements enhance birefringent properties.

25. The optical quantitative detection device as recited in claim 1 wherein birefringent property of a photonic band-gap crystal functions as an optical wave filter/detector and/or ray guide.

26. The optical quantitative detection device as recited in claim 1 wherein birefringent property of an ordered or disordered nano-structure of chalcopyrite material embedded in a linear/nonlinear composite generates coherent light over a broad wavelength range.

27. The optical quantitative detection device as recited in claim 1 wherein the nonlinear waveguide sensor further comprises a weak birefringent material and the birefringent effect is enhanced by embedding the material in a photonic band-gap crystal.

28. The optical quantitative detection device as recited in claim 1 wherein the optical quantitative detection device is adapted to detect an air borne indication of the target molecule.

29. The optical quantitative detection device as recited in claim 1 further comprises:
  a plurality of sensor elements; each sensor element sensitized for a particular molecular structure;
  an optical waveguide optically coupled to the plurality of sensor elements enabling optical excitation of the plurality of sensor elements; and
  a plurality of detectors wherein each one of the plurality of detectors is optically coupled to a corresponding one of the plurality of sensor elements;
  wherein optical excitation of the plurality of sensor elements enables discrimination of a target molecule.

* * * * *